United States Patent [19]
Warnking et al.

[11] Patent Number: 5,269,306
[45] Date of Patent: Dec. 14, 1993

[54] LITHOTRITOR COMPRISING A COUPLING DETECTOR

[75] Inventors: Rienhard Warnking; Sorin Grünwald, both of Solingen, Fed. Rep. of Germany

[73] Assignee: Dornier Medizintechnik GmbH

[21] Appl. No.: 924,647

[22] Filed: Aug. 6, 1992

[30] Foreign Application Priority Data
Aug. 6, 1991 [DE] Fed. Rep. of Germany ....... 4125950

[51] Int. Cl.$^5$ ............................................. A61B 17/22
[52] U.S. Cl. ........................... 128/660.03; 128/24 EL; 128/660.07
[58] Field of Search ........ 128/24 AA, 24 EL, 660.01, 128/660.03, 660.07; 73/644

[56] References Cited
U.S. PATENT DOCUMENTS

| | | | |
|---|---|---|---|
| 4,603,702 | 8/1986 | Hwang et al. | 128/660.01 |
| 4,791,915 | 12/1988 | Barsotti et al. | 128/24 AA |
| 4,867,168 | 9/1989 | Stoor et al. | 128/660.01 |
| 5,058,569 | 10/1991 | Hassler et al. | 128/24 EL |

Primary Examiner—Ruth S. Smith
Attorney, Agent, or Firm—Evenson, McKeown, Edwards & Lenahan

[57] ABSTRACT

A process for detecting the quality of the coupling of a shock wave therapy head of an extracorporal shock wave lithotritor to the patient's body. A comparison is made between an ultrasonic image taken without any coupling (blank image) and the actual ultrasonic image taken while the patient's body was coupled.

4 Claims, 2 Drawing Sheets

LITHOTRITOR COMPRISING A COUPLING DETECTOR

BACKGROUND OF THE INVENTION

This invention relates to a process for sensing the quality of the coupling between the therapy head of an extracorporal shock wave lithotritor and the body of the patient being treated.

In extracorporal shock wave lithotrity (ESWL), the patient's body is coupled to the therapy head of the shock wave therapy unit by means of a water cushion. When the coupling is insufficient, shock waves are reflected back into the therapy head on water-air transition areas, which can result in damage to the in-line sonic head of an ultrasonic locating device arranged in the therapy head. In addition, when the coupling is insufficient, the effectiveness of the therapy is substantially impaired, which represents avoidable stress to the patient.

German Patent Document DE 39 13 023 A1 discloses a crushing-wave treatment unit in which an ultrasonic image transducer is integrated into the crushing-wave therapy head. From ultrasonic images taken before and during the application of the crushing waves, subtraction images are generated in order to monitor the condition of the concrement to be destroyed.

In German Patent Document DE 39 00 893 A1, a shock wave treatment unit is disclosed in which the generation of a shock wave is prevented when the overlap between the object to be destroyed and the focal point of the shock wave therapy head is too small. For this purpose, overlap of the object to be destroyed, shown in an ultrasonic image and a focal-point zone marking brought into the ultrasonic image, is determined.

It is an object of the present invention to provide a process by means of which the quality of the coupling can be detected.

This object is achieved by the process according to the invention in which the sonic head of an ultrasonic locating device is integrated as an in-line sonic head in the therapy head of the lithotritor, and at least one ultrasonic image is taken when the patient's body is coupled. This ultrasonic image is then compared with an ultrasonic image which was taken when the patient's body was not coupled (that is, a "blank image" or "uncoupled image"). For this purpose, the comparison is based on those repeating echoes which are characteristic of an insufficient or non-existing coupling, and which are absent in the case of a proper coupling.

In the case of a defective coupling, warning signals may be generated, and the shock wave therapy unit may be automatically switched off, thus preventing reflection of the shock wave and unnecessary stress to the patient. Also, the life of the shock wave therapy and the integrated ultrasonic head are extended considerably.

Generation of shock waves in the therapy head may take place by means of known methods (including electromagnetic, piezoceramic and electrohydraulic processes).

Other objects, advantages and novel features of the present invention will become apparent from the following detailed description of the invention when considered in conjunction with the accompanying drawings.

DETAILED DESCRIPTION OF THE DRAWINGS

Figure 1:
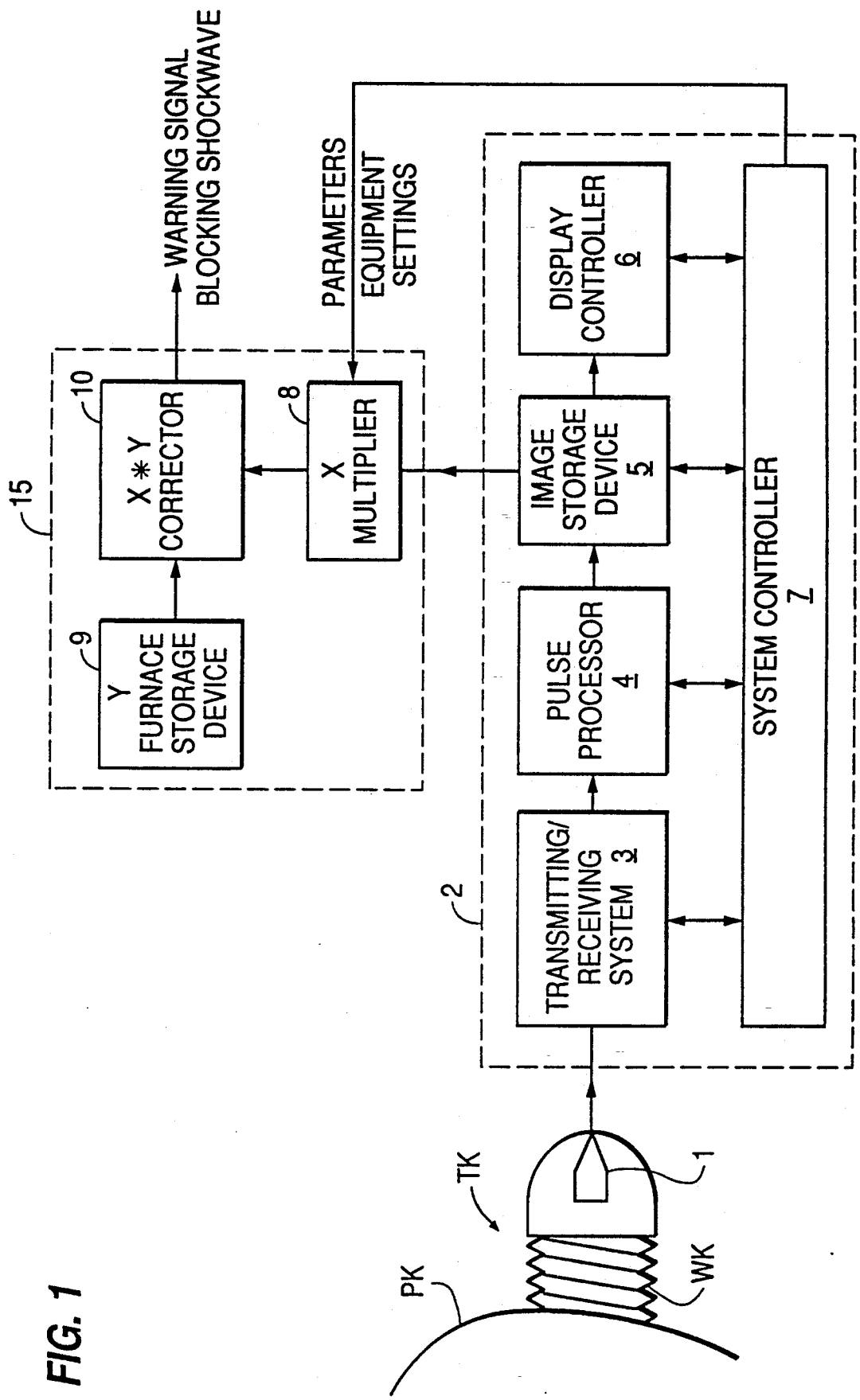
FIG. 1 is a diagram of a lithotritor arrangement for carrying out the process according to the invention.

FIG. 1 is a diagram of a lithotritor according to the invention. The therapy head TK, in which the shock waves are generated, is coupled to the patient's body PK by means of a water cushion WK. At least one sonic head 1 of an ultrasonic locating device 2 is used as an inline sonic head and is integrated into the therapy head TK.

A known prior art imaging ultrasonic diagnostic system is used as the ultrasonic locating device 2. It comprises the following main components:

Electronic transmitting/receiving system 3 (for controlling the transmission and reception functions of the ultrasonic transducing elements, focussing of the sound ray, and control of the sequential image design);

Pulse processor 4 (for filtering, demodulating and analog/digital conversion of the received signal);

Ultrasonic image storage 5 device (for taking the mean of the received signals for the purpose of signal/noise correction, and arranging the received signals in the desired imaging format);

Display controller 6 (for intermediate storage of the image content and conversion—read-out— in the TV format);

System controller 7 (for controlling the above main components of the ultrasonic locating device 2 corresponding to the equipment settings selected by the user).

The arrangement 15 for detecting the quality of the coupling (coupling detector) comprises:
a multiplier 8,
a correlator 10, and
an ultrasonic image storage device 9.

After an ultrasonic image has been taken by the ultrasonic locating device 2, the received signals are filtered, demodulated and converted to a digital code in pulse processor 4, with the digital data (ultrasonic frame) being stored in the ultrasonic image storage device 5. Thereafter they are read out of the image storage device 5, and the amplitude data of this ultrasonic frame (pixels) are weighted or scaled according to the parameters of the equipment settings of the ultrasonic locating device 2, particularly grey scale, zoom and power. This weighting takes place in the multiplier 8 and is used to compensate for different equipment settings. The weighted image content X is then compared with a reference image Y stored in the image storage device 9. The reference image Y stored in the image storage device 9 is a blank image, acquired while the patient's body PK is not coupled.

Figure 2A:
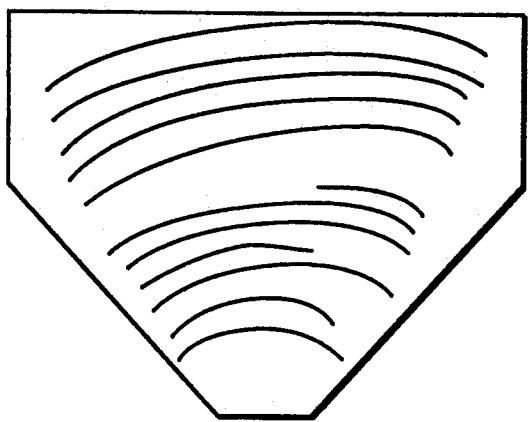
FIGS. 2a, 2b and 2c shows several outlined ultrasonic images of a patient's body, taken while the quality of the coupling is varied.
Figure 2B:
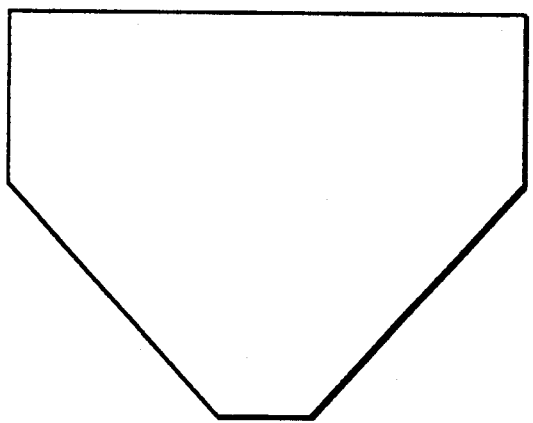
Figure 2C:
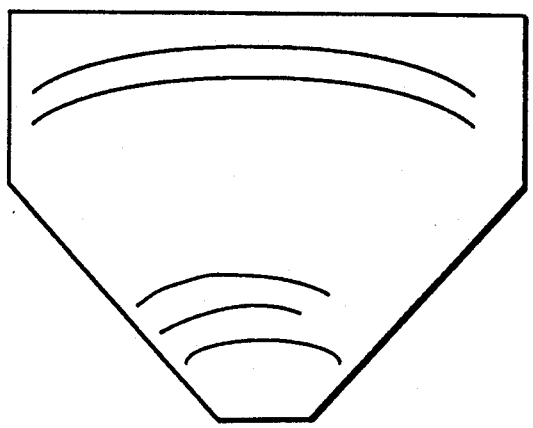

An example of such a blank image Y is illustrated in FIG. 2a. It shows characteristic repetition echoes which are recognizable in the image as stripes, and which do not exist when the patient is properly coupled (FIG. 2b). FIG. 2c illustrates the case of a partial coupling of the patient, which is insufficient for a successful therapy. It also has repetition echoes (which, however, are less pronounced here than in FIG. 2a).

In the correlator 10, the blank image Y from the image storage device 9 is compared in a known manner by means of statistical processes, with the actual ultrasonic image X which is weighted to account for the equipment setting parameters grey scale, zoom, power, in which case a spatial integration may take place, that is, by way of several pixels.

When a repetition pattern occurs in the actual image that has a pronounced similarity to that existing in the stored blank image Y, the correlator 10 generates a warning signal and blocks the further triggering of shock waves.

Although the invention has been described and illustrated in detail, it is to be clearly understood that the same is by way of illustration and example, and is not to be taken by way of limitation. The spirit and scope of the present invention are to be limited only by the terms of the appended claims.

We claim:

1. A method of evaluating the degree of coupling between a patient's body and a therapy head of a lithotritor for non-contact crushing of concrements in the patient's body, said lithotritor being of the type in which crushing waves are generated in the therapy head and are introduced into the patient's body by a coupling medium, comprising the steps of:

taking an uncoupled ultrasonic image by means of an ultrasonic locating device, a sonic head of which is integrated into the therapy head as an in-line sonic head when the therapy head is not coupled to the patient's body;

when the therapy head is coupled to the patient's body taking at least one coupled ultrasonic image by means of said ultrasonic locating device;

using statistical correlation processes to compare said coupled ultrasonic image with said uncoupled ultrasonic image to determine the extent to which characteristic repetition echoes present in said uncoupled ultrasonic image are also present in said coupled ultrasonic image; and evaluating the degree of coupling wherein the degree of coupling varies inversely to the extent to which characteristic repetition echoes present in said uncoupled ultrasonic image are also present in said coupled ultrasonic image.

2. A lithotritor for the non-contact crushing of concrements situated in a patient's body, comprising:

a therapy head in which crushing waves are generated and are introduced, by way of a coupling medium, into the patient's body, an ultrasonic locating device, a sonic head of which, is integrated into the therapy head as an in-line sonic head, a transmitting/receiving system, for controlling the transmission and reception functions of ultrasonic transducing elements; in said sonic head and an arrangement for evaluating the degree of coupling between the therapy head and the patient's body, said arrangement comprising:

an ultrasonic image storage device, for storing an uncoupled ultrasonic image received by the transmitting/receiving system and taken while the patient's body is not coupled to the therapy head;

a multiplier coupled to said image storage device, in which a coupled ultrasonic image received by the transmitting/receiving system and taken while the patient's body is coupled to the therapy head, is weighted according to equipment settings of the ultrasonic locating device;

a correlator coupled to said multiplier, in which the coupled ultrasonic image, weighted according to the parameters of equipment settings, is compared using statistical correlation processes with the uncoupled ultrasonic image and evaluated to determine the degree of coupling;

which varies inversely to the extent to which characteristic repetition echoes of the uncoupled ultrasonic image are present when the patient's body is coupled to the therapy head.

3. A lithotritor according to claim 2, further comprising a warning signal generator controlled by the correlator, which generates a warning signal when insufficient coupling is detected.

4. A lithotritor for non-contact crushing of concrements situated in a patient's body comprising:

a therapy head for generating crushing shock waves, said therapy head having a sonic locating device with a sonic head integrated into said therapy head, as an in-line sonic head;

means for coupling said therapy head to the patient's body;

means for receiving reflected ultrasonic signals from said shock waves and for processing said reflected ultrasonic signals to generate digital ultrasonic image data thereof, said means for receiving including means for scaling said reflected ultrasonic signals to compensate for variable operating parameters of said lithotritor;

means for storing ultrasonic image data taken while said therapy head is not coupled to the patient's body;

means for comparing, using statistical correlation processes, ultrasonic image data taken when said therapy head is coupled to the patient's body, with said stored ultrasonic image data to determine the extent to which characteristic repetition echoes present in said stored data are present in said ultrasonic image data taken when said therapy head is coupled to the patient's body; and means for evaluating the degree of comparison wherein the degree of comparison varies inversely to the extent to which characteristic repetition echoes present in said stored data are also present in said ultrasonic image data taken when said therapy head is coupled to the patient's body.

* * * * *